United States Patent [19]

Hoentjen et al.

[11] 4,204,060
[45] May 20, 1980

[54] NOVEL MONOCHLORO-S-TRIAZINE DERIVATIVES

[75] Inventors: Gerrit Hoentjen, Westervoort; Stephanus A. G. de Graaf, Renkum; Albert H. Bijkerk, Rheden; Cornelis R. H. I. de Jonge, De Steeg, all of Netherlands

[73] Assignee: Akzona Incorporated, Asheville, N.C.

[21] Appl. No.: 818,371

[22] Filed: Jul. 25, 1977

Related U.S. Application Data

[63] Continuation-in-part of Ser. No. 651,086, Jan. 21, 1976, abandoned.

[30] Foreign Application Priority Data

Oct. 4, 1974 [NL] Netherlands .................. 7511696

[51] Int. Cl.$^2$ .................................................. C07D 251/26
[52] U.S. Cl. ........................... 544/218; 260/45.8 NT
[58] Field of Search .............................. 544/218, 219

[56] References Cited

U.S. PATENT DOCUMENTS

| | | | |
|---|---|---|---|
| 2,936,227 | 5/1960 | Gysin et al. | 544/218 |
| 3,127,399 | 3/1964 | Lundberg | 544/218 |
| 3,245,992 | 4/1966 | Dexter et al. | 544/219 |
| 3,316,263 | 4/1967 | Ross et al. | 544/219 |
| 3,644,410 | 2/1972 | Gregg et al. | 544/219 |
| 3,729,471 | 4/1973 | Robin et al. | 544/219 |

FOREIGN PATENT DOCUMENTS

| | | |
|---|---|---|
| 2051521 | 4/1971 | Fed. Rep. of Germany ........... 544/218 |
| 1094577 | 12/1967 | United Kingdom . |
| 1268565 | 3/1972 | United Kingdom . |
| 1270254 | 4/1972 | United Kingdom . |
| 1393551 | 5/1975 | United Kingdom . |

OTHER PUBLICATIONS

Taylor et al., Chem. Abstracts, vol. 77, 7342m (1972).
Ohta et al., Chem. Abstracts, vol. 78, 16985w (1973).
Kuz'mina et al., Chemical Abstracts, vol. 77, entry 126580 (1972).

Primary Examiner—John M. Ford
Attorney, Agent, or Firm—Francis W. Young; Robert F. Green

[57] ABSTRACT

Novel monochloro-s-triazine derivatives of the formula:

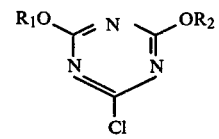

wherein $R_1$ and $R_2$ are independently alkyl or substituted alkyl of 6 to 20 carbon atoms, alkenyl having 6 to 20 carbon atoms, cycloalkyl having 6 carbon atoms, or furfuryl, and which derivatives provide antioxidants and UV stabilizers for polymers such as polyolefins are prepared by reacting an alcohol with cyanuric chloride in the presence of an acid acceptor having a $pK_b \leq 3$, in an organic solvent which is inert to the reaction components.

4 Claims, No Drawings

NOVEL MONOCHLORO-S-TRIAZINE DERIVATIVES

This application is a continuation-in-part of application Ser. No. 651,086, filed Jan. 21, 1976, now abandoned.

BACKGROUND OF THE INVENTION

The invention relates to novel monochloro-s-triazine derivatives and processes for the preparation of these compounds.

Cyanuric chloride has for a long time been considered a valuable starting material for preparing polymer additives, because it permits combining in one molecule both the functional groups and the compatibility enhancing groups.

Up to now the most commonly used intermediates containing said compatibility enhancing groups have been the dialkyl, the dialkylthio and the bis mono- or dialkylamino derivatives. However, the preparation of the first-mentioned compounds used to be cumbersome, whereas the other compounds are liable to degradation in the polymer.

It has now been found that these drawbacks may be obviated by the use of a previously unknown class of compounds.

General Description of the Invention

According to one aspect of this invention, there are provided novel compounds having the general formula:

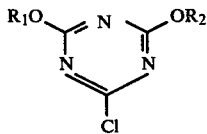

wherein $R_1$ and $R_2$ signify an organic group of which the two carbon atoms bonded to the oxygen atoms shown in said formula do not form part of an aromatic system and which groups each contain at least 6 carbon atoms.

The groups $R_1$ and $R_2$ independently of each other may represent a substituted or a non-substituted alkyl group with 6 to 20 carbon atoms, an alkenyl group with 6 to 20 carbon atoms, a cycloalkyl group with 6 carbon atoms or furfuryl.

Suitable substituents to be considered as including all groups that do not have any unfavorable influence on the stabilizing effect of the final additive and that do not interfere with the preparation of the present compounds. As suitable substituents may be mentioned fluorine, chlorine, bromine, or iodine, alkyl having from 1 to 4 carbon atoms, alkoxy having from 1 to 8 carbon atoms or aryl having from 6 to 9 carbon atoms. Some examples of triazine derivatives according to the invention are listed below:
(1) 2,4-dioctoxy-6-chloro-s-triazine
(2) 2,4-difurfuroxy-6-chloro-s-triazine
(3) 2,4-dicyclohexoxy-6-chloro-s-triazine
(4) 2-octoxy-4-stearoxy-6-chloro-s-triazine
(5) 2,4-dilauroxy-6-chloro-s-triazine
(6) 2,4-distearoxy-6-chloro-s-triazine According to another aspect of this invention, there is provided a process for the preparation of monochloro-s-triazine derivatives according to the foregoing formula wherein $R_1$ and $R_2$ have the meaning of an organic group of which the two carbon atoms bonded to the oxygen atoms shown in said figure do not form part of an aromatic system, which process comprises reacting an alcohol with cyanuric chloride in the presence of an acid acceptor and subsequently isolating the resulting reaction product from the reaction mixture.

A process of the type indicated above is known for the preparation of 2-chloro-4,6-dimethoxy-s-triazine from an article by O. Diels et al. in Ber., 36, 3191 (1903). In such process 1 molar equivalent of cyanuric chloride in the presence of 2 molar equivalents of sodium carbonate is reacted with a very large excess of methanol which also acts as a solvent. After heating with refluxing, cooling, and diluting with water the crude reaction product can be filtered off.

According to an article by J. R. Dudley et al. in the J. Am. Chem. Soc., 73, 2986 (1951), however, 2,4-dialyloxy-6-chloro-s-triazine cannot be prepared in this way (p. 2989, column 2, lines 28–31).

The present invention provides a process which makes it possible in a technologically attractive way to achieve the preparation of compounds according to the above formula, where $R_1$ and $R_2$ each have the meaning given above.

The invention is characterized in that in the above-indicated known process:
(a) for the acid acceptor a compound is used having a $pK_b \leq 3$;
(b) for the molar ratio of acid acceptor to cyanuric chloride a value of at least two is chosen;
(c) for the molar ratio of alcohol to cyanuric chloride a value of about two is chosen;
(d) the reaction is carried out in a solvent which is inert to the components of the reaction mixture.

It should be added that for the preparation of alkoxy-s-triazines the use of an acid acceptor having a $pK_b \leq 3$ is known in itself from the aforementioned article by J. R. Dudley et al. (p. 2989, column 1, lines 9–37). In that case, however, the process comprises the preparation of trialkyl cyanurates or trialkoxy-s-triazines.

The molar ratio of acid acceptor, for instance sodium hydroxide, to cyanuric chloride is then three. If under the reaction conditions described in said article this ratio is reduced to two, then not only the desired 2,4-dialkoxy-6-chloro-s-triazine is obtained but a large proportion of the reaction product is found to consist of the mono-alkoxy compound.

The abovementioned method of preparation is carried out using a large excess of alcohol and in the presence of the practically stoichiometrical proportion of acid acceptor required. However, also the use of an excess of acid acceptor in the presence of the practically stoichiometrical proportion of alcohol required is known from the aforementioned article by J. R. Dudley et al. There it is used for the preparation of a trialkoxy-s-triazine, more particularly of tris-(cyanomethyl)cyanurate. As acid acceptor pyradine (pKb=8.8) is used and the molar ratio of alcohol to cyanuric chloride is slightly higher than 3. If the last-mentioned ratio is reduced to about 2, then according to the present invention when as alcohol stearyl alcohol is used, only the monoalkoxy compound is formed in a small amount.

The process according to the invention can be carried out with all kinds of monofunctional alcohols, provided that the above-stated criterion is satisfied. They may be provided or not with substituents that are not influenced by the conditions of the reaction.

Because of the wide scope of application of these compounds it is preferred to use a process in which for $R_1$ and/or $R_2$ an aliphatic alcohol with 8 to 20 carbon atoms is used.

For use in the process according to the invention a choice may be made from a variety of inert solvents. Favorable results may be obtained if for the inert solvent either dioxane, tetrahydrofuran, dimethoxyethane, di-n-butyl ether, toluene, benzene, acetone, methyl isobutyl ketone, methyl ethyl ketone, is used. Because of toxicity and hazards presented by peroxide it is preferred that use be made of acetone or methyl ethyl ketone. They, however, have the disadvantage that slightly colored end-products may form as a result of condensation reactions under the influence of a strongly alkaline acid acceptor.

The invention therefore provides a process in which for the inert solvent methyl isobutyl ketone is preferably used. This solvent is little toxic, not liable to be formed into a peroxide, and resistant to the influence of a strongly alkaline medium; it has favorable physical properties (boiling point, heat of evaporation) and is available in large quantities and at a relatively low price.

For the acid acceptor any substance may be used having a $pK_b \leq 3$. In view of possible consecutive reactions the process should be carried out in the absence of water. Favorable results may be obtained when use is made of one or more of the following bases: potassium hydroxide, calcium oxide, borax, trisodium phosphate, tripotassium phosphate. Both in view of the cost and also because of further properties it is preferred to use NaOH in an anhydrous powdered form.

As in the process according to the invention one molar equivalent of cyanuric chloride is brought into reaction with two molar equivalents of alcohol, it will be necessary that for the bonding of the HCl liberated also use is made of two molar equivalents of acid acceptor. As the acid acceptor usually does not or only partly dissolves in the reaction medium and the reaction takes place partly at the surface of the heterogeneous phase, it is preferred that the process be carried out starting from a relatively large quantity. This quantity, of course, very much depends on the physical form of the acid acceptor. For instance, when use is made of a very finely powdered NaOH, a smaller quantity will be required than when use is made of NaOH granules.

Most acid acceptors that are suitable to be employed in the process according to the invention being strongly hygroscopic, it has the additional advantage that the resulting water reaction is bonded, so that it can no longer react with the end product or with cyanuric chloride to form a hydroxy-s-triazine. The molar ratio of alcohol to cyanuric chloride must not be chosen considerably higher than two in order to avoid the risk of the formation of a trialkoxy-s-triazine.

Particularly, if the reaction is carried out using a higher alcohol such as lauryl alcohol or stearyl alcohol, it is preferred to make use of a slightly short measure of alcohol. In this way the desired end product and the trialkoxy compound and/or the alcohol are no longer difficult to separate.

The temperature at which the process according to the invention can be carried out successfully is generally in the range of $-5°$ to $50°$ C. At higher temperatures the side reaction of cyanuric chloride or the end product with the water of reaction liberated will become too considerable. The most favorable reaction temperature is in the range of $15°$ to $30°$ C. Although the reaction still proceeds satisfactorily at $0°$ C., the reaction time will then be relatively long.

The reaction being highly exothermic, it is recommended that the acid acceptor be gradually added to the available reaction mixture.

As mentioned above, the alcohols that can be used in the process according to the invention may carry various substituents, provided that they are not influenced by the conditions of the reaction.

Some examples of alcohols that may be successfully used for carrying out the process according to the invention are listed in the following table.

TABLE n-hexyl alcohol
cyclohexanol
capryl alcohol
lauryl alcohol
myristyl alcohol
stearyl alcohol
benzyl alcohol
furfuryl alcohol
ω-bromo-octanol
$HO(CH_2CH_2O)_{4-10}H$
2-ethyl hexanol
methylol cyclohexane The process according to the invention can, of course, also be carried out starting from mixtures of alcohols. It should, however, be borne in mind that the reactivities of the various alcohols may rather differ. The isolation of the resulting reaction product from the reaction mixture and its further purification may be carried out in various ways known from chemical technology. For instance, the reaction mixture obtained, insofar as it is miscible with water, may be incorporated in a water-immiscible solvent and subsequently be washed with water. After drying, the solvent can be evaporated and the residue further purified by, for instance, recrystallization from an appropriate solvent.

The monochloro-s-triazines prepared by the process according to the present invention form very valuable intermediates. This is particularly true if for $R_1$ and $R_2$ aliphatic groups with at least 8 carbon atoms are taken. These monochloro-s-triazines provide anti-oxidants and UV-stabilizers which can readily be incorporated in the polymers, mainly polyolefins, to be stabilized. This cannot be said of the known UV-stabilizers described, for instance, in The Canadian Pat. No. 823 219, The German Pat. No. 2 307 777, or the U.S. Pat. No. 3,867,445. The compounds mentioned in all these patents are difficult to incorporate into a polymer of an olefinic character as a result of the absence of sufficient aliphatic groups or are far less resistant to the influence of UV-light or oxidation as a result of the aliphatic groups being bonded to the triazine ring by way of a nitrogen or a sulphur atom. The antioxidants, UV-stabilizers and all other compounds that are derived from the monochloro-s-triazines of the present invention show an unprecedentedly high resistance to oxidation and UV-radiation and they can readily be incorporated in all kinds of oligomers and polymers of an olefinic character.

DESCRIPTION OF THE PREFERRED EMBODIMENT

The invention will be elucidated in the following examples. The examples are, of course, given by way of illustration and should not be interpreted as limitative of the present invention.

EXAMPLE I

Preparation of 2,4-dioctoxy-6-chloro-s-triazine (using dioxane as solvent)

To a solution of 18.4 g (0.1 mole) of cyanuric chloride and 26.0 g (0.2 moles) of octanol in 200 ml of dioxane were added 9.0 g (0.225 moles) of powdered sodium hydroxide over a period of 20 minutes at a reaction temperature in the range of 32° to 37° C. After 7 hours the reaction mixture was poured into 500 ml of petroleum ether (boiling point 40°–60° C.). The solution thus obtained was washed with water, dried with MgSO$_4$ and the solvent evaporated.

The 2,4-dioctoxy-6-chloro-s-triazine was obtained in the form of an oil (26 g). Calculated on the amount of octanol used, the yield was 70%.

EXAMPLE II

Preparation of 2,4-dioctoxy-6-chloro-s-triazine (using methyl isobutyl ketone as solvent).

To a solution of 92 g (0.5 moles) of cyanuric chloride and 118 g (0.9 moles) of octanol in 1000 ml of methyl isobutyl ketone (MIBK) were added 72 g (1.8 moles) of powdered sodium hydroxide over a period of 30 minutes at a reaction temperature in the range of 25° to 30° C. Already after 50 minutes the reaction was found to be completed. The reaction mixture was acidified with concentrated hydrochloric acid and heated to 70° C., after which the NaCl was filtered off. The solution was subsequently dried over MgSO$_4$ and boiled down by evaporation.

The 2,4-dioctoxy-6-chloro-s-triazine was obtained in the form of an oil and had a melting point in the range of 8° to 11° C. Calculated on the amount of octanol used, the yield was 75%.

EXAMPLE III

Preparation of 2,4-dilauroxy-6-chloro-s-triazine.

To a solution of 18.4 g (0.1 mole) of cyanuric chloride and 38.0 g (0.2 moles) of lauryl alcohol in 200 ml of dioxane there were added 9.9 g (0.25 moles) of powdered sodium hydroxide over a period of 10 minutes at a reaction temperature in the range of 25° to 45° C. After 3 hours the reaction mixture was found to be converted. The reaction mixture was poured into chloroform and further treated as indicated in Example I. After evaporation there were obtained 30.4 g of a white, solid substance which upon recrystallization from ethanol yielded 29.1 g of a pure 2,4-dilauroxy-6-chloro-s-triazine having a melting point in the range of 43.5°–44.9° C.

EXAMPLE IV

Preparation of 2,4-distearoxy-6-chloro-s-triazine.

To a solution of 18.4 g (0.1 mole) of cyanuric chloride and 48.5 g (0.18 moles) of stearyl alcohol in 300 ml of methyl isobutyl ketone (MIBK) were added 14.4 g (0.36 moles) of powdered sodium hydroxide over a period of 10 minutes at a reaction temperature in the range of 25° to 30° C. After 45 minutes the reaction was completed. After it had been acidified with concentrated hydrochloric acid and heated to 80° C., the reaction mixture was freed from NaCl by filtration. Upon cooling the reaction mixture to below 15° C., the 2,4-distearoxy-6-chloro-s-triazine completely crystallized out.

Calculated on the amount of stearyl alcohol used, the yield was 89%. After recrystallization from acetone to remove traces of stearyl alcohol a product was obtained having a melting point in the range of 70.5°–71.5° C.

EXAMPLE V (Comparative Experiment)

In this example it is shown that the preparation of 2,4-distearoxy-6-chloro-s-triazine cannot be realized with a weakly alkaline acid acceptor such as pyridine. To a solution of 18.4 g (0.1 mole) of cyanuric chloride and 54.0 g (0.2 moles) of stearyl alcohol in 250 ml of dry acetone there were slowly added dropwise, with vigorous stirring, 20 g (0.25 moles) of pyridine at a reaction temperature of 5° C. Subsequently, the reaction mixture was allowed to stand for 16 hours at 20° C., after which the entire mixture was poured into ice water.

After acidification with concentrated hydrochloric acid the solid matter was filtered off, washed with water, dried and subsequently boiled in methyl isobutyl ketone (MIBK). With thin layer chromatographic analysis only the presence of a large proportion of stearyl alcohol and a small proportion of monostearoxy-dichlorotriazine could be demonstrated.

What is claimed is:
1. 2,4-Distearoxy-6-chloro-s-triazine.
2. 2,4-Difurfuroxy-6-chloro-s-triazine.
3. 2,4-Dicyclohexoxy-6-chloro-s-triazine.
4. 2-Octoxy-4-stearoxy-6-chloro-s-triazine.

* * * * *